US010251918B2

(12) United States Patent
Ashida et al.

(10) Patent No.: US 10,251,918 B2
(45) Date of Patent: Apr. 9, 2019

(54) PREVENTIVE OR THERAPEUTIC AGENT FOR RUMINANT ANIMAL MASTITIS

(71) Applicant: ASAHI CALPIS WELLNESS CO., LTD., Shibuya-ku, Tokyo (JP)

(72) Inventors: Nobuhisa Ashida, Kanagawa (JP); Tomokazu Imabayashi, Kanagawa (JP); Hisashi Aso, Miyagi (JP)

(73) Assignee: Asahi Calpis Wellness Co., Ltd., Tokyo (JP)

( * ) Notice: Subject to any disclaimer, the term of this patent is extended or adjusted under 35 U.S.C. 154(b) by 0 days.

(21) Appl. No.: 14/891,533

(22) PCT Filed: May 16, 2014

(86) PCT No.: PCT/JP2014/063055
§ 371 (c)(1),
(2) Date: Nov. 16, 2015

(87) PCT Pub. No.: WO2014/185516
PCT Pub. Date: Nov. 20, 2014

(65) Prior Publication Data
US 2016/0120919 A1    May 5, 2016

(30) Foreign Application Priority Data
May 17, 2013    (JP) .................. 2013-105425

(51) Int. Cl.
*A61K 35/742*    (2015.01)
*A23K 50/10*    (2016.01)
(Continued)

(52) U.S. Cl.
CPC ............ *A61K 35/742* (2013.01); *A23K 1/009* (2013.01); *A23K 1/1813* (2013.01); *A23K 10/18* (2016.05); *A23K 50/10* (2016.05)

(58) Field of Classification Search
None
See application file for complete search history.

(56) References Cited

U.S. PATENT DOCUMENTS 4,919,936 A * 4/1990 Iwanami ................. C12R 1/125
424/442

FOREIGN PATENT DOCUMENTS

AU    624356 B    11/1989
AU    624356 B2    11/1992
(Continued)

OTHER PUBLICATIONS

Fossum "Isolation of Bacillus subtilis in connection with bovine mastits", Nordisk Veterinaermedicin, 1986 38(4), 233-236, Abstract (Year: 1986).*
(Continued)

*Primary Examiner* — Robert J Yamasaki
*Assistant Examiner* — Charles Zoltan Constantine
(74) *Attorney, Agent, or Firm* — Foley & Lardner LLP

(57) ABSTRACT

The present invention relates to a substance or method for preventing or treating mastitis in ruminant animals, particularly in dairy cows. Specifically provided are: a preventive or therapeutic agent, a feed additive, a feed, and a pharmaceutical composition for ruminant animal mastitis, characterized by comprising, as an active ingredient, a *Bacillus* genus bacterium having the property of being capable of increasing or maintaining $CD11c^+$ $CD172a^+$ blood dendritic cell gate 2 in cows.

8 Claims, 1 Drawing Sheet

(51) Int. Cl.
  *A23K 10/18* (2016.01)
  *A23K 1/00* (2006.01)
  *A23K 1/18* (2006.01)

(56) References Cited

FOREIGN PATENT DOCUMENTS

| CN | 101253934 A | 9/2008 |
|---|---|---|
| CN | 102550857 A | 7/2012 |
| EP | 0287699 A2 | 10/1988 |
| EP | 0363491 A1 | 4/1990 |
| EP | 2545930 A1 | 1/2013 |
| JP | 64-086842 A | 3/1989 |
| JP | 02-503800 A | 11/1990 |
| JP | 11-285378 A | 10/1999 |
| JP | 2001-224317 A | 8/2001 |
| JP | 2006-514642 A | 5/2006 |
| JP | 2008-074787 A | 4/2008 |
| JP | 2012-502920 A | 2/2012 |
| JP | 2012-126657 A | 7/2012 |
| TW | 201136528 A | 11/2011 |
| WO | WO 2004/054538 A1 | 7/2004 |
| WO | WO 2006/117019 A1 | 11/2006 |
| WO | WO 2008/069102 A1 | 6/2008 |
| WO | WO 2010/033714 A1 | 3/2010 |
| WO | WO 2011/111783 A1 | 9/2011 |
| WO | WO 2011/115306 A1 | 9/2011 |

OTHER PUBLICATIONS

International Search Report dated Jul. 29, 2014, in PCT/JP2014/063055.
Al-Qumber et al., "Commensal bacilli inhibitory to mastitis pathogens isolated from the udder microbiota of healthy cows," Journal of Applied Microbiology, 2006, 101:1152-1160.
Ikuta et al., "Efficacy of a Dietary Supplementation of Microbial Product to Prevent Mastitis during the Early Lactation Period in Dairy Cows," Hyogo Kenritsu Norin Suisan Gijutsu Sogo Center Kenkyu Hokoku Chikusan Hen, 2009, 45:13-17, with English summary on first page.
Nissan Johhoh (Nissan Information), vol. 34, Aug. 2006, Nissan Gosei Kogyo Co., Ltd., 2 pages, with partial English translation.
Saito, Yasunori, Journal of Clinical Veterinary Medicine, Sep. 2010, 28(9):19-22, with partial English translation.
Sato et al., "Effect of *Bacillus subtilis* Preparation on the Blastogenic Activity of Peripheral Blood Lymphocytes in Cows," Kachiku Rinshoshi, 2006, 29(1):6-9, with English abstract on first page.
Office Action dated Nov. 14, 2017, in JP 2015-517139.
BioFood™-A, 2011, http://www.keihansangyo.co.jp/wp-content/uploads/2011/03/biofood.pdf, 2 pages, with 1 page English translation.
Supplementary European Search Report dated Feb. 13, 2017, in EP 14797064.4.
Bjoerck et al., "Cutting Edge: CD19+ Pro-B Cells Can Give Rise to Dendritic Cells In Vitro," The Journal of Immunology, Dec. 1, 1998, 161(11):5795-5799.
Drakes et al., "Bacterial Probiotic Modulation of Dendritic Cells," Infection and Immunity, Jun. 2004, 72(6):3299-3309.
Hart et al., "Modulation of human dendritic cell phenotype and function by probiotic bacteria," Gut, Nov. 1, 2004, 53(11):1602-1609.
Li et al., "Novel activity evaluation and subsequent partial purification of antimicrobial peptides produced by *Bacillus subtilis* LFB112," Ann. Microbiol., 2012, 62:667-674.

* cited by examiner

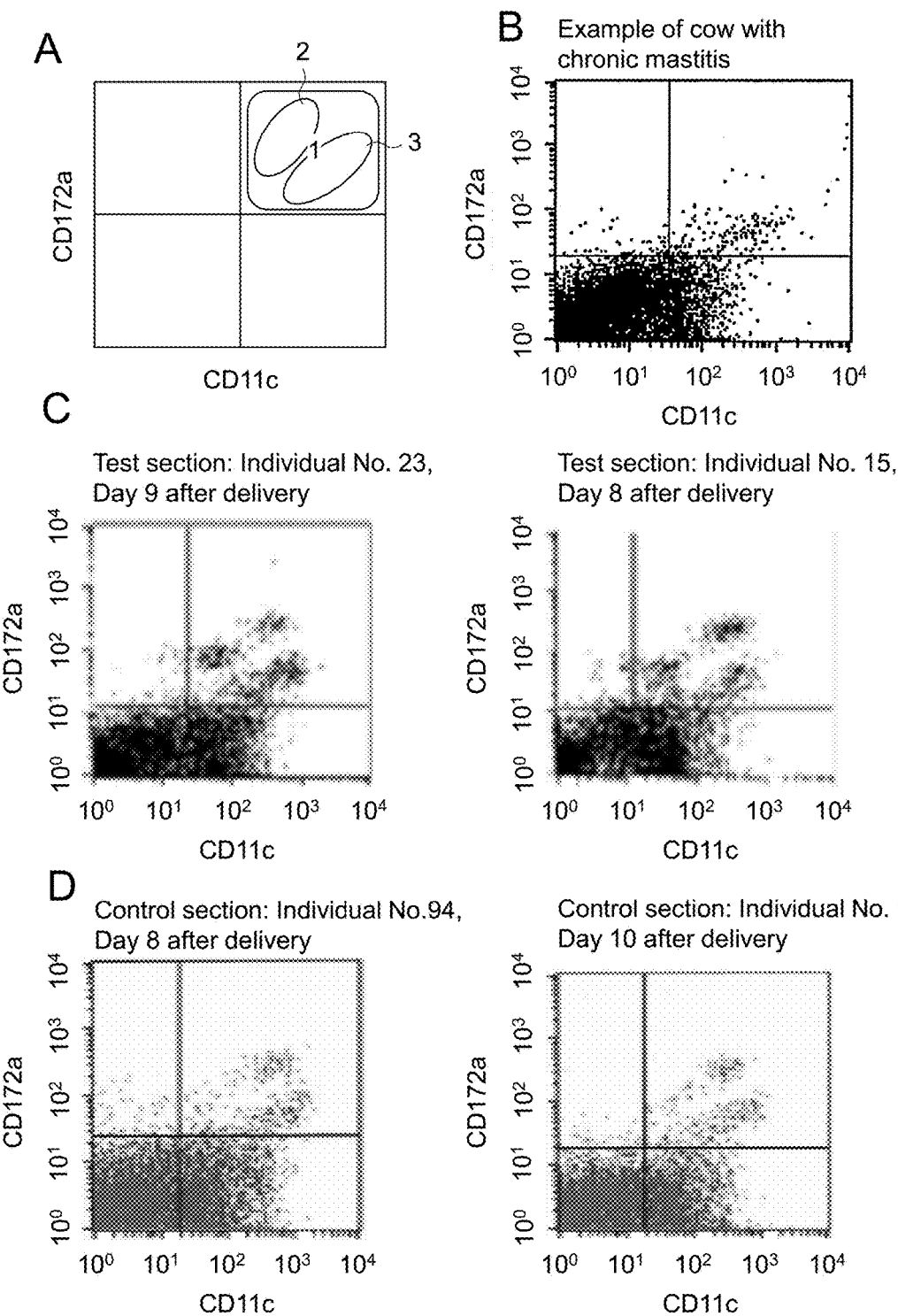

PREVENTIVE OR THERAPEUTIC AGENT FOR RUMINANT ANIMAL MASTITIS

TECHNICAL FIELD

The present invention relates to a preventive or therapeutic agent, a feed additive, a feed, or a pharmaceutical composition for the prevention or therapy of mastitis in ruminant animals, such as cows, comprising *Bacillus* genus bacteria having a certain property as an active ingredient.

BACKGROUND ART

Mastitis is the inflammation of mammary tissues, and most of its causes are due to the infection of bacteria, such as *Staphylococcus aureus, Escherichia coli, Streptococcus*, and *Pseudomonas aeruginosa*. Particularly, mastitis in cows is an important problem for dairy farmers, as described below.

Mastitis is roughly divided into clinical mastitis and subclinical mastitis (also referred to as nonclinical mastitis). In the clinical mastitis, macroscopic abnormalities, such as the red swelling, fever, and pain of the breast or the contamination of milk with clots are observed, whereas in the subclinical mastitis, inflammation occurs in the mammary gland without abnormalities as in clinical mastitis. The subclinical mastitis is much higher in the percentage of occurrence, and about 25 to 50% of milking cows are said to suffer from the disease.

As to the onset of mastitis in cows, it is the present situation that there is not taken a sufficient countermeasure of prevention of mastitis before onset or therapy of cows affected with mastitis, which is a large problem in the milk industry. According to "the number of cows having disease accidents classified by disease types" reported in Statistical Tables of Livestock Mutual Relief, 2009 in Japan, 30% of about 1,410,000 cows had urinary diseases, of which around 90 percent had mastitis. Also in the number of cows having death or disuse accidents classified by disease types, 9% of about 160,000 had urinary diseases. Thus, in fiscal year 2009 alone, cows affected with mastitis were about 420,000 in number, and the number of discarded cows amounts to 15,000. In addition, the onset of mastitis reduces milk quality and milk yield, resulting in incalculable economic loss. Therapy for mastitis is carried out by administering antibiotics; however, such therapy does not often result in a complete cure and there is at present no method other than isolation. Even if the antibiotic administration led to a complete cure, milk during its administration cannot be shipped; thus, economic loss due to mastitis is said to be estimated to be about one hundred billion yen in Japan. In addition to the direct economic loss, the labor load and the prescription charge associated with the therapy of cows infected with mastitis are not negligible. Further, side effects are conceivable, such as that dairy cows once having the onset of mastitis have an extremely high probability of having the onset of mastitis during the subsequent lactation period after delivery and that dairy cows affected with mastitis have delayed estrus. As such, in addition to a means for prevention or effective therapy of mastitis being sought in the milk industry, there is an urgent need for the establishment of a technique for preventing, or suppressing the recurrence of, mastitis.

Various proposals have previously been made for the prevention or therapy of mastitis in ruminant animals, such as cows. Among these proposed preventive or therapeutic agents, some examples using microorganisms for the prevention or therapy of mastitis have been in particular reported.

For example, Patent Literature 1 discloses a composition for the prevention or therapy of mastitis in cows, comprising a culture composition obtained from a culture of a microorganism belonging to the genus *Aureobasidium* as an active ingredient.

Patent Literature 2 discloses a composition for the prevention or therapy of livestock mastitis, comprising viable baker's yeast cells or their contents as an active ingredient.

Other examples of the use of a viable bacterial agent in dairy cows include the use of Natokin-L (lactic acid bacterium and *Bacillus subtilis*), Miyairi bacterial powder (butyric acid bacterium), Biosuri (lactic acid bacterium, saccharifying bacterium, and butyric acid bacterium), and Bovactin (lactic acid bacterium and butyric acid bacterium) for the prevention/therapy of simple diarrhea (Non Patent Literature 1). Table 2 in this literature describes that the incidence of mastitis was decreased by the use of a viable bacterial agent; however, it is not shown what the viable bacterial agent was. In this connection, among the viable bacterial agents listed in Table 1 of the literature, "Biosuri" is now used in 80 to 90% of the cases of viable bacterial agent administration to dairy cows; thus, the viable bacterial agent used in Table 2 is presumed to be probably "Biosuri". Viable bacteria agents including Biotop (*Bacillus subtilis*) are known to have effects, such as drastically decreasing the occurrence of tympania, stimulating appetite, and rendering the hair glossy, as well as effects, such as decreasing the number of cows excreting *Salmonella* (Non Patent Literature 2).

In addition, the same applicant as the applicant of this application teaches the use of viable cells of *Bacillus subtilis* as an agent for improving the efficiency of feed utilization for ruminant animals (Patent Literature 3). The improvement of the utilization efficiency in this literature is the improvement of the efficiency of digestion absorption, which improves milk yield and milk quality in dairy cows. The same applicant as the applicant of this application also teaches a feed additive prepared by mixing *Bacillus subtilis* strain C-3102 with vitamins, minerals, amino acids, and the like (Patent Literature 4). Furthermore, Patent Literature 5 describes the use of *Bacillus subtilis* for reducing the growth of enteric pathogenic bacteria in animals, such as ruminant animals. However, Patent Literatures 3, 4, and 5 do not describe that *Bacillus subtilis* is useful for the prevention and therapy of mastitis in cows.

PRIOR ART LITERATURE

Patent Literature

Patent Literature 1
JP Patent Publication (Kokai) No. 2012-126657 A
Patent Literature 2
JP Patent Publication (Kokai) No. 2001-224317 A
Patent Literature 3
International Publication WO 2011/115306
Patent Literature 4
JP Patent Publication (Kokai) No. 64-86842 A (1989)
Patent Literature 5
JP Patent Publication (Kohyo) No. 2012-502920 A Non Patent Literature Non Patent Literature 1
Yasunori Saito, Journal of Clinical Veterinary Medicine, September 2010, vol. 28, no. 9
Non Patent Literature 2
Nissan Johhoh (Nissan Information), vol. 34, August 2006, Nissan Gosei Kogyo Co., Ltd.

SUMMARY OF INVENTION

Problem to be Solved by Invention

As described in the Background Art, there is strong need for a means for the prevention or effective therapy of cow mastitis in the milk industry.

Thus, an object of the present invention is to provide an agent or pharmaceutical composition or a method for the prevention and/or therapy of cow mastitis.

Means for Solving Problem

The present inventors have now found that certain *Bacillus* genus bacteria exert a mastitis preventive effect by being provided (or, administered or ingested) to cows, especially dairy cows and further that the bacteria enhance a therapeutic effect on mastitis after onset.

Thus, the present invention encompasses the following features.

[1] A preventive or therapeutic agent for ruminant animal mastitis, comprising, as an active ingredient, a *Bacillus* genus bacterium having the property of (1) described below:

(1) being capable of increasing or maintaining $CD11c^+$ $CD172a^+$ blood dendritic cell gate 2 in a cow.

[2] The preventive or therapeutic agent according to [1], wherein the *Bacillus* genus bacterium further has the property of (2) described below:

(2) having a *Bifidobacterium*-growing activity of more than 0.8 when the *Bifidobacterium*-growing activity of *Bacillus subtilis* strain C-3102 (international accession number: FERM BP-1096) is set at 1.

[3] The preventive or therapeutic agent according to [1] or [2], wherein the *Bacillus* genus bacterium has the property of (3) described below:

(3) having protease and amylase activities of more than 0.7 when both of the protease activity and the amylase activity of *Bacillus subtilis* strain C-3102 (international accession number: FERM BP-1096) are set at 1.

[4] The preventive or therapeutic agent according to any one of [1] to [3], wherein the *Bacillus* genus bacterium has the property of (4) described below:

(4) being capable of achieving the prevention or therapy of mastitis when orally administered to a cow at a dose of $1 \times 10^5$ cells/day/animal or more.

The preventive or therapeutic agent according to any one of [1] to [4], wherein the ruminant animal is a cow.

[6] The preventive or therapeutic agent according to any one of [4] to [5], wherein the oral administration in the property (4) is carried out for a period from 1 month before cow delivery to 3 months after the delivery.

[7] The preventive or therapeutic agent according to any one of [1] to [6], wherein the *Bacillus* genus bacterium is a *Bacillus subtilis* bacterium.

[8] The preventive or therapeutic agent according to [7], wherein the *Bacillus subtilis* bacterium is *Bacillus subtilis* strain C-3102 (international accession number: FERM BP-1096), or a variant of the strain C-3102 having the property (1), the properties (1) and (2), the properties (1) and (3), the properties (1) to (3), the properties (1) and (4), the properties (1), (3), and (4), or the properties (1) to (4).

[9] A feed additive for the prevention or therapy of ruminant animal mastitis, comprising the preventive or therapeutic agent according to any one of [1] to [8] as an active ingredient.

[10] The feed additive according to [9], further comprising an antibiotic for the therapy of mastitis.

[11] A feed having an enhanced preventive or therapeutic effect on ruminant animal mastitis, comprising an effective amount of the feed additive according to [9] or [10] for the prevention or therapy of the ruminant animal mastitis.

[12] A method for enhancing a preventive or therapeutic effect of a feed for ruminant animals on ruminant animal mastitis, comprising adding an effective amount of the feed additive according to [9] or [10] for the prevention or therapy of the ruminant animal mastitis to the feed for ruminant animals.

[13] A pharmaceutical composition for the prevention or therapy of ruminant animal mastitis, comprising a *Bacillus* genus bacterium as an active ingredient, having the property of (1) described below:

(1) being capable of increasing or maintaining $CD11c^+$ $CD172a^+$ blood dendritic cell gate 2 in a cow, in combination with a pharmaceutically acceptable carrier.

[14] The pharmaceutical composition for the prevention or therapy according to [13], wherein the *Bacillus* genus bacterium further has the property of (2) described below:

(2) having a *Bifidobacterium*-growing activity of more than 0.8 when the *Bifidobacterium*-growing activity of *Bacillus subtilis* strain C-3102 (international accession number: FERM BP-1096) is set at 1.

[15] The pharmaceutical composition for the prevention or therapy according to [13] or [14], wherein the *Bacillus* genus bacterium has the property of (3) described below:

(3) having protease and amylase activities of more than 0.7 when both of the protease activity and the amylase activity of *Bacillus subtilis* strain C-3102 (international accession number: FERM BP-1096) are set at 1.

[16] The pharmaceutical composition for the prevention or therapy according to any one of [13] to [15], wherein the *Bacillus* genus bacterium has the property of (4) described below:

(4) being capable of achieving the prevention or therapy of mastitis when orally administered to a cow at a dose of $1 \times 10^5$ cells/day/animal or more.

[17] The pharmaceutical composition according to any one of [13] to [16], wherein the ruminant animal is a cow.

[18] The pharmaceutical composition according to any one of [13] to [17], wherein the cow is a healthy dairy cow, a dairy cow with the risk of onset of mastitis, a dairy cow affected with mastitis, or a dairy cow having a history of mastitis.

[19] The pharmaceutical composition according to any one of [16] to [18], wherein the oral administration in the property (4) is carried out for a period from 1 month before cow delivery to 3 months after the delivery.

[20] The pharmaceutical composition according to any one of [13] to [19], wherein the *Bacillus* genus bacterium is a *Bacillus subtilis* bacterium.

[21] The pharmaceutical composition according to [20], wherein the *Bacillus subtilis* bacterium is *Bacillus subtilis* strain C-3102 (international accession number: FERM BP-1096), or a variant of the strain C-3102 having the property (1), the properties (1) and (2), the properties (1) and (3), the properties (1) to (3), the properties (1) and (4), the properties (1), (3), and (4), or the properties (1) to (4).

[22] The pharmaceutical composition according to any one of [13] to [21], further comprising an antibiotic for the therapy of mastitis.

[23] A method for the prevention or therapy of mastitis in a ruminant animal, comprising administering or providing the preventive or therapeutic agent according to any one of [1] to [8], the feed additive according to [9] or [10], the feed according to [11], or the pharmaceutical composition according to any one of [13] to [22] to a ruminant animal in need thereof.

[24] The method according to [23], further comprising administering an antibiotic for the therapy of mastitis, if necessary.

Effect of Invention

The present invention provides *Bacillus* genus bacteria having a certain property, having a highly preventive or therapeutic effect in the prevention or therapy of mastitis in ruminant animals, preferably cows, more preferably dairy cows. Even after the symptoms are ameliorated by antibiotic therapy, dairy cows having a history of mastitis are known to have an extremely high probability of the onset of mastitis after each subsequent delivery; however, the preventive or therapeutic agent of the present invention provides the unexpected efficacy, i.e., that when orally administered or fed to the cows from 1 month before delivery, the agent can effectively suppress the subsequent onset of mastitis in the cows and can, in most cases, render the cows into a completely symptom-free condition.

BRIEF DESCRIPTION OF DRAWINGS

FIG. 1 This FIGURE shows the panels demonstrating an increase in $CD11c^+$ $CD172a^+$ blood dendritic cell gate 2 in cows which is correlated with the effect of the *Bacillus subtilis* bacterium used as an active ingredient in the present invention on amelioration of mastitis. Panel A schematically shows the approximate positions or areas of CD11c-positive CD172a-positive blood dendritic cell gate 2 (when mastitis is ameliorated, expression intensities of both CD172a and CD11c increase) and gate 3 (the expression intensity of CD172a is lower when compared to the cell gate 2) which are detected within gate 1 in the first quadrant (upper right). Panel B shows the results of the dual color flow cytometric analysis of $CD11c^+$ $CD172a^+$ blood dendritic cells in cows with chronic mastitis (control), and panel C shows the results of the dual color flow cytometric analysis of $CD11c^+$ $CD172a^+$ blood dendritic cells in the dairy cows of the test section to which the preventive or therapeutic agent of the present invention was administered (cow number 23: day 9 after delivery (left) and cow number 15: day 8 after delivery (right)). Panel D shows the results of the dual color flow cytometric analysis of $CD11c^+$ $CD172a^+$ blood dendritic cells in control dairy cows to which the *Bacillus subtilis* bacterium was not administered (cow number 94: day 8 after delivery (left) and cow number 902: day 10 after delivery (right)).

MODE FOR CARRYING OUT INVENTION

The present invention will be described below in more detail.

1. Preventive or Therapeutic Agent

The present invention provides a preventive or therapeutic agent for ruminant animal mastitis, comprising a *Bacillus* genus bacterium having a certain property as described below, preferably a *Bacillus subtilis* bacterium, as an active ingredient.

The mastitis, the *Bacillus* genus bacteria, and the preventive agent will be described below.

[1] Mastitis

The mastitis used herein is mastitis in ruminant animals, preferably cows, more preferably dairy cows, and this disease includes clinical mastitis and subclinical mastitis (also referred to as nonclinical mastitis). As described in the Background Art above, in the clinical mastitis, macroscopic abnormalities, such as the red swelling, fever, and pain of the breast or the contamination of milk with clots are observed, whereas in the subclinical mastitis, inflammation occurs in the mammary gland without abnormality as in clinical mastitis. The subclinical mastitis is much higher in the percentage of occurrence, and about 25 to 50% of milking cows are said to suffer from the disease. The clinical mastitis is easily completely cured by antibiotic medication, while the subclinical mastitis is intractable and has no effective cure, and thus the only means is to take measures, such as isolating an infected animal.

Particularly, in dairy cows having the onset of the above mastitis, especially subclinical mastitis, the milk secretion amount and the milk quality are reduced and the use of a chemotherapeutic agent such as an antibiotic makes the milk shipment impossible, causing large economic loss.

The preventive or therapeutic agent of the present invention is effective against not only clinical mastitis but also subclinical mastitis. Because no effective remedy for the prevention or therapy of subclinical mastitis has previously been reported, the preventive or therapeutic agent or the like of the present invention is important in the dairy (milk) industry.

As used herein, the term "ruminant animal" includes livestock animals, such as cows, goats, and sheep. Particularly, ruminant animals secreting/producing milk, for example, cows and goats are preferable. The cows are preferably dairy cows (for example, Holstein species, Jersey species, Guernsey species, Ayrshire species, Kerry species, Dairy Shorthorn species, Red Danish Species, and Simmental species), especially healthy dairy cows, dairy cows with the risk of onset of mastitis, dairy cows affected with mastitis, or dairy cows having a history of mastitis. The preventive agent of the present invention is effective especially for healthy dairy cows, dairy cows with the risk of onset of mastitis, or healthy dairy cows having a history of mastitis, and can be used as a therapeutic agent in dairy cows affected with mastitis.

[2] *Bacillus* Genus Bacteria

The preventive or therapeutic agent of the present invention comprises, as an active ingredient, a *Bacillus* genus bacterium having the properties (1) and optionally (2), as described below:

(1) the *Bacillus* genus bacterium is capable of increasing or maintaining $CD11c^+$ $CD172a^+$ blood dendritic cell gate 2 in a cow, and (2) the *Bacillus* genus bacterium has a *Bifidobacterium*-growing activity of more than 0.8 when the *Bifidobacterium*-growing activity of *Bacillus subtilis* strain C-3102 (international accession number: FERM BP-1096) is set at 1.

Any of the *Bacillus* genus bacteria having the properties of (1) and optionally (2) above can be used as an active ingredient of the preventive or therapeutic agent of the present invention.

For the above property (1), $CD11c^+$ $CD172a^+$ blood dendritic cells are antigen-presenting cells, and CD11c-positive and CD172a-positive cells moving through the blood and regulating local immunity. These cells can be separated as CD11c-positive and CD172a-positive cells by a magnetic activated cell sorting system (MACS method) using magnetic bead-bound anti-CD11c antibody and magnetic bead-bound anti-CD172a antibody and a MACS separation column after collecting a lymphocyte population from the peripheral blood by specific gravity centrifugation (2,300 rpm, 30 minutes) using Lympholyte-H and further separating monocytes, B cells, and T cells, and the CD11c$^+$ CD172a$^+$ blood dendritic cells can further be analyzed by a dual color flow cytometry method. The findings were observed that the CD11c$^+$ CD172a$^+$ blood dendritic cells consisted of 2 characteristic cell populations shown within gate 1 in the first quadrant in Panel A of FIG. 1 (gates 2 and 3) and among these cell populations, particularly the gate 2 was decreased in cows affected with, or having not recovered from, mastitis and increased in cows having recovered from, or not having the onset of, the disease by administering the *Bacillus subtilis* bacterium of the present invention; thus, it was found, for the first time, that the CD11c$^+$ CD172a$^+$ blood dendritic cells were correlated with the presence or absence of the onset of, or the presence or absence of recovery from, mastitis.

From the above findings, it is thought that when exposure to bacteria or the like causing mastitis occurs at a period when the risk of having the onset of mastitis is high (a period within 3 months after delivery, especially within about 1 month after delivery), an increase in the CD11c$^+$ CD172a$^+$ blood dendritic cell gate 2 prevents mastitis. In other words, the preventive or therapeutic agent of the present invention increases the CD11c$^+$ CD172a$^+$ blood dendritic cell gate 2 of a subject for administration depending on the environment (for example, situation of contact to bacteria or injury). Conversely, for cows affected with mastitis, the CD11c$^+$ CD172a$^+$ blood dendritic cell gate 2 cannot be increased for the period of the disease. Stated another way, as used herein, the "being capable of increasing or maintaining CD11c$^+$ CD172a$^+$ blood dendritic cell gate 2" as one of the properties of *Bacillus* genus bacteria, such as *Bacillus subtilis*, means increasing, or maintaining, at a high level, the proportion of the CD11c$^+$ CD172a$^+$ dendritic cell gate 2 to total blood dendritic cells of an animal of interest compared to its proportion at the onset of mastitis at a period when the risk of having the onset of mastitis is high, thereby forming an immune environment suitable for preventing the onset of mastitis.

For the above property (2), the *Bacillus subtilis* usable in the present invention has a feature that it has a *Bifidobacterium*-growing activity of more than 0.8, preferably more than 0.9, more preferably 1 or more, when the *Bifidobacterium*-growing activity of *Bacillus subtilis* strain C-3102 (international accession number: FERM BP-1096) is set at 1. The *Bifidobacterium*-growing activity has an aspect associated with immune enhancement and has not previously been reported to be associated with a dendritic cell-growing activity; however, if the *Bacillus subtilis* has capacity equivalent (on the order of 80%) to or higher than the *Bifidobacterium*-growing activity of *Bacillus subtilis* strain C-3102, it is expected to have a preventive or therapeutic effect on mastitis through the dendritic cell-growing activity.

The *Bacillus subtilis* bacterium usable in the present invention can further have the properties of (3) and/or (4) described below:

(3) the *Bacillus subtilis* bacterium has protease and amylase activities of more than 0.7 when both of the protease activity and the amylase activity of *Bacillus subtilis* strain C-3102 (international accession number: FERM BP-1096) are set at 1, and/or (4) the *Bacillus subtilis* bacterium is capable of achieving the prevention or therapy of mastitis when orally administered to a cow at a dose of $1\times10^5$ cells/day/animal or more.

For the property (3), the *Bacillus* genus bacteria usable in the present invention have a feature that they can prevent or ameliorate mastitis when orally administered to cows at a dose of $1\times10^6$ cells/day/animal or more, preferably $1\times10^7$ cells/day/animal or more, more preferably $1\times10^8$ cells/day/animal or more, still more preferably $1\times10^9$ cells/day/animal or more, most preferably $6\times10^9$ cells/day/animal or more. Here, the dose is the number of viable cells of *Bacillus* genus bacteria ingested per day per animal, and ingestion into an animal can be performed once daily or a plurality of times, for example, 2 to 4 times daily in divided doses. The oral administration is carried out for a period from 1 month before cow delivery to 3 months after the delivery, and the presence of recovery from, or amelioration of, mastitis can be confirmed by using an increase in CD11c$^+$ CD172a$^+$ blood dendritic cells, particularly the gate 2 shown in FIG. 1, in the peripheral blood, as an indicator, or by determination based on findings from diagnosis by an animal doctor.

For the property (4), the *Bacillus* genus bacteria can have a feature that they have protease and amylase activities of more than 0.7, preferably more than 0.8, more preferably more than 0.9, most preferably 1 or more, when both of the protease activity and the amylase activity of *Bacillus subtilis* strain C-3102 (international accession number: FERM BP-1096) are set at 1. The protease activity and the amylase activity can be measured by a method as described, for example, in Examples described below. Among *Bacillus* genus bacteria known as viable bacteria agents, *Bacillus subtilis*, for example, *Bacillus subtilis* strain C-3102, has high protease and amylase activities (see Table 3 described below).

Examples of the *Bacillus* genus bacteria having the properties of (1) and optionally (2) include *Bacillus subtilis* bacteria, *Bacillus licheniformis* bacteria, and *Bacillus amyloliquefaciens* bacteria. Specific examples thereof include *Bacillus subtilis* strain C-3102 (international accession number: FERM BP-1096), variants of the strain C-3102 having the property (1), the properties (1) and (2), the properties (1) and (3), the properties (1) to (3), the properties (1) and (4), the properties (1), (3), and (4), or the properties (1) to (4), and *Bacillus subtilis* type strains. The *Bacillus* genus bacteria are preferably *Bacillus subtilis* strain C-3102 and variants of the strain C-3102.

*Bacillus subtilis* strain C-3102 was domestically deposited on Dec. 25, 1985 in International Patent Organism Depositary, National Institute of Advanced Industrial Science and Technology at Tsukuba Central 6, 1-1-1 Higashi, Tsukuba, Ibaraki, Japan (post code: 305-8566) [at deposit, 1-1-3 Higashi, Yatabe, Tsukuba, Ibaraki, Japan (post code: 305)] under Accession No. FERM P-8584, and has been transferred to the international deposit on Jun. 28, 1986 in the same institute under Accession No. FERM BP-1096 (at the time of transfer) (JP Patent Publication (Kokai) No. 62-232343 A (1987)). The strain C-3102 is also marketed under the trade name "Calsporin™" by the present applicant.

The variant of *Bacillus subtilis* strain C-3102 can be obtained by artificially inducing the mutation of the strain, for example, by culture under irradiation with high energy ray, such as ultraviolet light or X-ray, or by culture in the presence of a mutagen, such as nitrosoguanidine, N-ethyl-N-nitrosourea, or nitrosamine, isolating a variant colony, and further, performing verification that the variant is a mutant, for example, by comparing the nucleotide sequence of rDNA (commonly used for bacterial classification) of the variant with the sequence of strain C-3102, and confirming that the variant has the property (1), the properties (1) and (2), the properties (1) and (3), the properties (1) to (3), the properties (1) and (4), the properties (1), (3), and (4), or the properties (1) to (4).

The *Bacillus* genus bacteria usable in the present invention may be used directly in the form of its culture; or, if necessary, the bacteria may be obtained as a dried product by separating or concentrating bacterial cell components by a separation means, such as centrifugation or filtration, followed by using, for example a drying method, such as lyophilization, vacuum thermal drying, or spray drying. *Bacillus subtilis* can be cultured under culture conditions conventional for those skilled in the art.

The medium for culturing *Bacillus subtilis* contains at least carbon source, nitrogen source, and inorganic salts.

Examples of the carbon source include saccharides, such as sorbitol, glucose, starch, dextrin, cyclodextrin, amylose, amylopectin, pullulan, oligosaccharides, glycerin, and malt extract or wort. These carbon sources may be used singly or in a mixture of two or more.

Examples of the nitrogen source include organic nitrogen compounds, such as meat extract, malt extract, yeast extract, peptone, polypeptone, protein hydrolysate, powdered soy bean, milk casein, amino acids, and corn steep liquor, and/or ammonium salts, such as ammonia, ammonium nitrate, ammonium sulfate, and ammonium chloride, nitrates, such as sodium nitrate, and inorganic nitrogen compounds, such as urea. The nitrogen sources may be used singly or in a mixture of two or more.

The inorganic salts may be, for example, phosphate, hydrochloride, sulfate, and acetate of magnesium, manganese, calcium, sodium, potassium, copper, iron, and zinc.

The medium may be a commercial medium or a nutrient broth.

The culture may be carried out under well-known culture conditions. The culture temperature is typically 20 to 45° C., preferably 35 to 42° C., and the pH of the medium suitable for the culture is typically 6.0 to 9.0, preferably 6.5 to 8.5; however, the conditions are not limited to these ranges.

[3] Preventive or Therapeutic Agent

The preventive or therapeutic agent of the present invention contains a *Bacillus* genus bacterium (viable cells), preferably *Bacillus subtilis* bacterium, more preferably *Bacillus subtilis* strain C-3102 or its variant, having the property (1), the properties (1) and (2), the properties (1) and (3), the properties (1) to (3), the properties (1) and (4), the properties (1), (3), and (4), or the properties (1) to (4), as an active ingredient.

The content of *Bacillus* genus bacterium or bacteria in the preventive agent is typically 0.001 to 95.0% by weight, for example, 0.1 to 40% by weight in terms of dried bacterial cells; and the preventive agent may contain, for example, $1 \times 10^5$ to $6 \times 10^9$ cells or more of the bacterium or bacteria.

The preventive or therapeutic agent is for oral administration or feeding and is in the form of a solid, a semi-solid, or a liquid; specifically, the agent is in the form of powders, granules, pills, pellets, tablets, capsules, or the like for the solid, in the form of a gel or the like for the semi-solid, and in the form of a suspension or the like for the liquid. In addition to the bacterial cells as an active ingredient, the preventive or therapeutic agent may contain substances for prescription to a formulation, for example, a carrier (e.g., an excipient or a diluent) and optionally an additive or additives.

Examples of the carrier can include lactose, mannitol, sorbitol, xylitol, microcrystalline cellulose, starch, dicalcium phosphate, purified water, gelatin, agar, sodium alginate, and carrageenan.

Examples of the additive include, but not limited to, a binder, a disintegrator, a lubricant, a filler, a slip additive, a surfactant, an antioxidant, a fungicide, and a thickener.

Examples of the binder include sodium starch glycolate, tragacanth gum, acacia, polyvinylpyrrolidone, corn starch, gelatin, powdered cellulose, microcrystalline cellulose, sorbitol, starch, polyvinylpyrrolidone, copolymers of vinylpyrrolidone and vinyl derivatives, hydroxypropylcellulose, and hydroxypropylmethylcellulose.

Examples of the disintegrator include corn starch, potatostarch, sodium starch glycolate, carboxymethylcellulose sodium, carboxymethylcellulose calcium, croscarmellose sodium, crospovidone, polyvinylpyrrolidone, methylcellulose, microcrystalline cellulose, lower alkyl-substituted hydroxypropyl cellulose, pregelatinized starch, and sodium alginate.

Examples of the lubricant include magnesium stearate, stearic acid, polyethylene glycol, talc, and silica.

Examples of the slip additive include silicon dioxide, talc, calcium stearate, zinc stearate, sodium stearyl fumarate, and magnesium stearate.

Examples of the surfactant include sodium lauryl sulfate and polysorbate 80.

Examples of other components include amino acids, vitamins, minerals, dyes (astaxanthin, canthaxanthin, and the like), and enzymes (e.g., amylase, protease, xylanase, cellulase, β-glucanase, and lipase).

The total content of the carrier and the additive in the preventive or therapeutic agent is the value obtained by subtracting the content percentage (%) of the active ingredient (dried bacterial cells) from 100%.

The preventive or therapeutic agent of the present invention can be used for the prevention and, in some instances, therapy of mastitis in a ruminant animal, preferably a cow, more preferably a dairy cow.

The prevention of mastitis can be performed by orally administering or feeding *Bacillus* genus bacterium or bacteria, such as *Bacillus subtilis* bacterium or bacteria, having the above property or the properties at a dose of $1 \times 10^5$ to $6 \times 10^9$ cells/day or more to a cow, such as a dairy cow during the period from at least 1 month before delivery to 3 months after delivery. When administered or fed, the bacterium or bacteria can be administered at a total dose of $1 \times 10^5$ to $6 \times 10^9$ cells/day or more, once daily or several times daily in divided doses, for example, 2 times in morning and evening each day, or the preventive agent at such a dose can be fed by being mixed in a feed, a drink, or the like. For example, when Calsporin™ is fed to cows, 40 g ($1.5 \times 10^8$ CFU)/day of Calsporin powder can be provided, for example, in doses of 20 g in the morning and 20 g in the evening, by mixing it in a feed. For cows such as dairy cows, particularly, a coarse feed, such as hay, or a concentrated feed is often provided as a feed; thus, the preventive agent is preferably mixed in these feeds. For a cow for administration, the agent can be administered or fed to the cow having the experience of the onset of mastitis in the past to markedly suppress the onset of mastitis in the cow in which the onset of mastitis is expected.

2. Feed Additive and Feed

The present invention further provides a feed additive containing the above preventive or therapeutic agent.

The feed additive of the present invention can be produced by mixing the preventive or therapeutic agent with other approved optional components constituting the feed additive so that the additive contains an effective amount of the above-defined *Bacillus* genus bacterium or bacteria, such as *Bacillus subtilis* bacterium or bacteria, for preventing ruminant animal mastitis. Here, the effective amount of *Bacillus* genus bacterium or bacteria, such as *Bacillus subtilis* bacterium or bacteria, is such an amount that the animal can ingest $1\times10^5$ to $6\times10^9$ cells/day or more of the bacteria.

A feed additive is generally a substance for imparting a desired function to an animal feed; in the case of the present invention, the function is to conduct the prevention or therapy, suppression, or mitigation of mastitis in ruminant animals, particularly cows, more preferably dairy cows.

The feed additive can further contain an antibiotic for the therapy of mastitis. For example, "Kachiku Kyosai Yakkohbetsu Yakka Kijun Hyo (The List of Drug Price Standards Classified by Drug Effects, Livestock Mutual Relief), Ver. 2011" lists, as antibiotics, antibiotics, such as cepham antibiotics, penicillin antibiotics, and macrolide antibiotics, which are effective against bacteria, such as *Staphylococcus aureus*, *Escherichia coli*, *Streptococcus*, and *Pseudomonas aeruginosa*, known as causative bacteria of mastitis, for example, antibiotics, such as erythromycin, oxytetracycline hydrochloride, dicloxacillin sodium, cefazolin, cefuroxime sodium, nafcillin sodium, benzylpenicillin procaine, dihydrostreptomycin sulfate, kanamycin sulfate, cephapirin sodium, monoammonium glycyrrhizinate, and cefalonium, or a mixture of a plurality of these antibiotics.

In addition to an active ingredient, the feed additive can contain components, such as a carrier (an excipient or a diluent) and an additive or additives, for forming the agent. The carrier and the additives are the above-exemplified ones used for producing the preventive or therapeutic agent of the present invention. The feed additive may have any of the forms of a solid, a semi-solid, and a liquid; it preferably has a solid form and can be produced, for example, in the shape of powders, granules, pills, pellets, tablets, and capsules.

The present invention further provides a method for enhancing a preventive or therapeutic effect on ruminant animal mastitis in a feed for ruminant animals, comprising adding an effective amount of the above-described feed additive for the prevention or therapy of the mastitis to the feed for ruminant animals.

For the therapy of mastitis in cows and other animals, therapeutic agents for mastitis listed in the "Kachiku Kyosai Yakkohbetsu Yakka Kijun Hyo (The List of Drug Price Standards Classified by Drug Effects)" (Japan Veterinary Products Association) have conventionally been used, and antibiotics are used as the main therapeutic agents; however, these agents have not prevented the recurrence of the disease. The preventive or therapeutic agent of the present invention or a feed additive containing the agent can complement the antibiotic therapy.

Because the preventive or therapeutic agent of the present invention has the above unique features, the present invention also relates to a feed having an enhanced preventive or therapeutic effect on ruminant animal mastitis, comprising an effective amount of the above-described feed additive or additives for the prevention or therapy of the ruminant animal mastitis.

Unlike known feeds, the feed of the present invention is characterized by comprising an effective amount of *Bacillus* genus bacterium or bacteria, such as *Bacillus subtilis* bacteria, for preventing ruminant animal mastitis. Known feeds before the filing of the present application have not been on the market for the prevention (or therapy) of mastitis because it has not been recognized that *Bacillus* genus bacterium or bacteria, such as *Bacillus subtilis* bacterium or bacteria, have a preventive (or therapeutic) action or effect on ruminant animal mastitis.

The feed includes coarse feeds mainly containing fiber (for example, soilage, dry grass, and silage rice straw) and concentrated feeds rich in starch and proteins (also referred to as a feed mixture) (for example, cereals, such as corn, soybean, rice bran, wheat bran, barley, and milo, and vegetable oil cakes, such as soybean oil cake, rapeseed oil cake, and cottonseed oil cake), and a proper mixture of these feed components is fed to ruminant animals, such as cows. In addition, vitamins (vitamins A, D3, E, B1, B2, B6, B12, C, and K3, inositol, biotin, pantothenic acid, niacin, choline, folic acid, and the like), amino acids, dietary salt, and other minerals can be added. For feed components, ones described, for example, in Japan Standard Feed Ingredients Chart (edited by National Agriculture and Food Research Organization, Japan) can also be used.

The feed preferably contains $1\times10^5$ to $6\times10^9$ cells/day or more of the *Bacillus subtilis* bacterium or bacteria in an amount ingestible by an animal; thus, the feed additive of the present invention can be mixed in a feed so as to provide such a bacterial cell amount.

3. Pharmaceutical Composition and Method for Prevention or Therapy of Mastitis

The present invention further provides a pharmaceutical composition for the prevention or therapy of ruminant animal mastitis, comprising a *Bacillus* genus bacterium, such as *Bacillus subtilis* bacterium, as an active ingredient, having the property (1), the properties (1) and (2), the properties (1) and (3), the properties (1) to (3), the properties (1) and (4), the properties (1), (3), and (4), or the properties (1) to (4), in combination with a pharmaceutically acceptable carrier.

The *Bacillus* genus bacterium, such as *Bacillus subtilis* bacterium, as an active ingredient is the same as the bacterium as the active ingredient of the preventive or therapeutic agent, and can be used as the active ingredient of the pharmaceutical composition of the present invention provided that it is a *Bacillus* genus bacterium, such as *Bacillus subtilis* bacterium, having the properties (1) and optionally (2), i.e., having the property of being capable of increasing $CD11c^+$ $CD172a^+$ cell gate 2 in the blood dendritic cells of a cow, such as a dairy cow, as the property (1) and, optionally, the property of having a *Bifidobacterium*-growing activity of more than 0.8, preferably more than 0.9, more preferably 1 or more, when the *Bifidobacterium*-growing activity of *Bacillus subtilis* strain C-3102 (international accession number: FERM BP-1096) is set at 1 as the property (2).

In addition to the properties (1) and optionally (2), the *Bacillus* genus bacterium, such as *Bacillus subtilis* bacterium, may have the property of having protease and amylase activities of more than 0.7, preferably more than 0.8, more preferably more than 0.9, most preferably 1 or more, when both of the protease activity and the amylase activity of *Bacillus subtilis* strain C-3102 (international accession number: FERM BP-1096) are set at 1 as the property (3), and/or the property of being capable of achieving the prevention or therapy of mastitis when orally administered to a cow at a dose of $1\times10^5$ to $6\times10^9$ cells/day/animal or more as the property (4).

In the present invention, the cow is, for example, a healthy dairy cow, a dairy cow with the risk of onset of mastitis, a dairy cow having a history of mastitis, or a dairy cow affected with mastitis. In these dairy cows, the composition of the present invention can achieve prevention or therapy. Furthermore, in a cow actually having the onset of mastitis, the composition of the present invention can be used for the therapy, or suppression, mitigation or amelioration of mastitis.

Examples of the *Bacillus* genus bacterium include *Bacillus subtilis* strain C-3102 (international accession number: FERM BP-1096), variants of the strain C-3102 having the above property or properties, and *Bacillus subtilis* type strains; however, any of the *Bacillus* genus bacteria may be a bacterium usable in the present invention provided that it is a *Bacillus* genus strain having the property (1), the properties (1) and (2), the properties (1) and (3), the properties (1) to (3), the properties (1) and (4), the properties (1), (3), and (4), or the properties (1) to (4).

The content of *Bacillus* genus bacterium or bacteria, such as *Bacillus subtilis* bacterium or bacteria, in the pharmaceutical composition of the present invention may be, for example, $1 \times 10^5$ to $6 \times 10^9$ cells or more as the bacterium or bacteria. The bacterium or bacteria are preferably administered to, or ingested by, an animal at a dose of $1 \times 10^5$ to $6 \times 10^9$ cells/day or more; thus, the composition can be orally administered or fed once daily or a plurality of times (for example, 2 to 4 times) daily in divided doses.

The pharmaceutical composition can optionally contain a therapeutic agent for mastitis (an antibiotic or the like). The therapeutic agent for mastitis may be any of the therapeutic agents for mastitis listed in the "Kachiku Kyosai Yakkohbetsu Yakka Kijun Hyo (The List of Drug Price Standards Classified by Drug Effects)" (Japan Veterinary Products Association); specifically, particular examples thereof include antibiotics, such as cepham antibiotics, penicillin antibiotics, and macrolide antibiotics, effective against bacteria, such as *Staphylococcus aureus, Escherichia coli, Streptococcus*, and *Pseudomonas aeruginosa*, known as causative bacteria of mastitis, for example, the above-exemplified antibiotics.

The pharmaceutical composition of the present invention is in the form of a solid, a semi-solid, or a liquid; specifically, the composition is in the form of powders, granules, pills, pellets, tablets, capsules, or the like for the solid, in the form of a gel or the like for the semi-solid, and in the form of a suspension or the like for the liquid. In addition to the bacterial cells as an active ingredient, the preventive agent may contain substances for prescription to a formulation, for example, a pharmaceutically acceptable carrier (e.g., an excipient or a diluent) and, in some instances, an additive or additives.

Examples of the carrier can include lactose, mannitol, sorbitol, xylitol, microcrystalline cellulose, starch, dicalcium phosphate, purified water, gelatin, agar, sodium alginate, and carrageenan.

Examples of the additive may include, but not limited to, a binder, a disintegrator, a lubricant, a filler, a slip additive, a surfactant, an antioxidant, a fungicide, and a thickener. These additives can be properly selected from the following and added to the composition.

Examples of the binder include sodium starch glycolate, tragacanth gum, acacia, polyvinylpyrrolidone, corn starch, gelatin, powdered cellulose, microcrystalline cellulose, sorbitol, starch, polyvinylpyrrolidone, copolymers of vinylpyrrolidone and vinyl derivatives, hydroxypropylcellulose, and hydroxypropylmethylcellulose.

Examples of the disintegrator include corn starch, potatostarch, sodium starch glycolate, carboxymethylcellulose sodium, carboxymethylcellulose calcium, croscarmellose sodium, crospovidone, polyvinylpyrrolidone, methylcellulose, microcrystalline cellulose, lower alkyl-substituted hydroxypropyl cellulose, pregelatinized starch, and sodium alginate.

Examples of the lubricant include magnesium stearate, stearic acid, polyethylene glycol, talc, and silica.

Examples of the slip additive include silicon dioxide, talc, calcium stearate, zinc stearate, sodium stearyl fumarate, and magnesium stearate.

Examples of the surfactant include sodium lauryl sulfate and polysorbate 80.

Examples of other components include amino acids, vitamins, minerals, dyes (e.g., astaxanthin and canthaxanthin), and enzymes (e.g., amylase, protease, xylanase, cellulase, β-glucanase, and lipase).

The present invention further provides a method for the prevention or therapy of mastitis in a ruminant animal, comprising orally administering or feeding the preventive or therapeutic agent, the feed additive, the feed, or the pharmaceutical composition to a ruminant animal in need thereof.

For the prevention or therapy of mastitis, *Bacillus* genus bacterium or bacteria, such as *Bacillus subtilis* bacterium or bacteria, are preferably given at a dose of $1 \times 10^5$ to $1 \times 10^6$ cells/day/animal or more, preferably $1 \times 10^7$ cells/day/animal or more, more preferably $1 \times 10^8$ cells/day/animal or more, still more preferably $1 \times 10^9$ cells/day/animal or more, most preferably $6 \times 10^9$ cells/day/animal or more, to a ruminant animal, such as a dairy cow during at least the period from 1 month before delivery to 3 months after delivery. For dosage form, the viable bacterial cells may be administered at the above dose per day as the total dose, once daily or several times daily in divided doses. In administering the pharmaceutical composition, the composition may be fed by being mixed in diets, such as feeds and drinks. For cows such as dairy cows, particularly, hay or a concentrated feed is often provided as a feed; thus, preferably the composition is mixed in these feeds. The cow, particularly the dairy cow, for administration is a healthy dairy cow, a dairy cow with the risk of onset of mastitis, or a dairy cow having a history of mastitis; the onset of mastitis can be markedly suppressed in these dairy cows, and the therapy or mitigation of mastitis can be achieved in a dairy cow affected with mastitis.

In a cow confirmed to have the onset of mastitis, the combination, if necessary, with an antibiotic (as described above) conventionally usable for its therapy can increase the rate of complete cure and could shorten the time to complete cure. An antibiotic effective against causative bacteria, such as *Staphylococcus aureus, Escherichia coli, Streptococcus*, or *Pseudomonas aeruginosa*, is administered to a cow affected with mastitis by a method, such as intravenous administration, intramuscular administration, or oral administration, while the pharmaceutical composition of the present invention can be administered to the animal before, during, or after the antibiotic administration.

The preventive or therapeutic agent, the feed additive, or the pharmaceutical composition is preferably administered or fed to an animal by mixing it in an animal feed, drink, or the like.

The agent is preferably administered or fed to an animal such that the viable bacterial dose is $1 \times 10^5$ to $1 \times 10^6$ cells/ day/animal or more, preferably $1\times10^7$ cells/day/animal or more, more preferably $1\times10^8$ cells/day/animal or more, still more preferably $1\times10^9$ cells/day/animal or more, most preferably $6\times10^9$ cells/day/animal or more.

EXAMPLES

The present invention will be described below further in detail with reference to Examples. However, these Examples are not intended to limit the technical scope of the present invention.

Example 1

<Treatment of Mastitis in Diary Cow>

Calsporin™ (Calpis Co., Ltd., Japan) (active ingredient: *Bacillus subtilis* strain C-3102 (FERM BP-1096), $1\times10^{10}$ cells/g) was fed to dairy cows having a history of mastitis (cow numbers 23 and 15) during the previous lactation period in the test section shown in Table 1 below, for the period from 1 month before delivery to 3 months after delivery, by mixing Calsporin at a viable bacterial dose of $6\times10^9$/day or more in a feed. As a feed, Rakunoh Kazoku Max (Zennoh Feed Mills of the Tohoku District Co, Ltd., Japan), Astroliner (vitamin preparation: Snow Brand, Japan), flaked corn, and a coarse feed (timothy, oats, dent corn silage, alfalfa hay cube) were fed during the lactation period, and a feed for the dry period (Trans-Pro, Snow Brand, Japan) and a coarse feed (timothy, oats) were fed during the dry period. In contrast, for dairy cows having a history of the onset of mastitis (cow numbers 94 and 902) in the control section shown in the same Table 1, Calsporin was not added to a feed.

Dairy cows having a history of mastitis during the previous lactation period are known to also have a high risk of having the onset of mastitis during the present period. The previous lactation period refers to a period from after the last delivery to 1 month before delivery during the present period; all of the dairy cows used in the present experiment are dairy cows having a history of mastitis 1 to 3 times during the previous lactation period, which are cows having received medication with antibiotics 6 to 23 times.

The results are shown in Table 1. In both of the cow nos. 15 and 23 of the test section, the results show that (1) the onset of mastitis was absent; (2) medication with an antibiotic was absent; and (3) the proportion of $CD11c^+$ $CD172a^+$ blood dendritic cell gate 2 to total dendritic cells was little increased or decreased and maintained at a high level compared to that for the control section during the test period in dendritic cell analysis. In contrast, both of the cow nos. 94 and 902 of the control section had the onset of mastitis, received therapy with antibiotics, and tended to transiently or chronically have a low proportion of $CD11c^+$ $CD172a^+$ blood dendritic cell gate 2 compared to that for the test section in dendritic cell analysis. Here, the results of measuring $CD11c^+$ $CD172a^+$ blood dendritic cell gate 2 are shown in FIG. 1 (panels C and D) and Table 2. The proportion of $CD11c^+$ $CD172a^+$ blood dendritic cell gate 2 to total dendritic cells definitely increased at 8 to 10 days after delivery in the test section compared to that in the control section. This suggests that the cows of the test section had immunity to attack bacteria causing mastitis when they were exposed to the bacteria or the like, in the period in which they have a high risk of mastitis after delivery (particularly, 8 to 10 days after delivery). In other words, the little increase or decrease and the as-needed increase of the proportion of $CD11c^+$ $CD172a^+$ blood dendritic cell gate 2 to total dendritic cells probably indicates that the administration of *Bacillus subtilis* strain C-3102 increased or maintained the immunity in the blood, protecting against the onset of mastitis. During the test period, the onset of mastitis was not observed in the test section, but once or twice in the control section, thereby necessitating therapy with antibiotics. The increase of $CD11c^+$ $CD172a^+$ blood dendritic cell gate 2 in the test section around 7 days after delivery (a stage when mastitis is most apt to occur) is an indicator showing that the preventive or therapeutic agent of the present invention (active ingredient: *Bacillus subtilis* strain C-3102) worked effectively for the prevention of mastitis.

TABLE 1

| | | Test Section | | Control Section | |
|---|---|---|---|---|---|
| | | Cow No.: 23 | Cow No.: 15 | Cow No.: 94 | Cow No.: 902 |
| Previous Lactation Period (Track Record) | Frequency of Onset of Mastitis | Once (1) | Once (1) | Twice (2) | Twice (2) |
| | Frequency of Medication | 14 | 11 | 23 | 6 |
| | Name of Administered Drug | Cefamezin, Homing | Cefamezin, Homing | Cefamezin, Homing, Mastritin | Cefamezin, Homing |
| Present Period (From 1 Month before Delivery to 3 Months after Delivery) | Frequency of Onset of Mastitis | Zero (0) | Zero (0) | Twice (2) | Once (1) |
| | Frequency of Medication | 0 | 0 | 6 | 3 |
| | Name of Administered Drug | None | None | Cefamezin, Homing | Cefamezin |
| | Evaluation by MACS Method* | ○ | ○ | X | X |

* In the evaluation by a MACS method, "○" refers to that the proportion of gate 2 is little increased or decreased and maintained at a high level during the test period in dendritic cell analysis as described in FIG. 1, and "X" refers to the presence of a period when the proportion of gate 2 is transiently or chronically low.

TABLE 2

Data by MACS Method

| | Blood Collection Period | | | | |
|---|---|---|---|---|---|
| | 1 | 2 | 3 | 4 | 5 |
| Blood Collection Day | From Day −24 before Delivery to Day 1 after Delivery | Day 8 to Day 10 after Delivery | Day 36 to Day 37 after Delivery | Day 60 to Day 65 after Delivery | Day 92 to Day 93 after Delivery |
| Individual No. 23 | 0.28 | 3.22 | 1.12 | 1.26 | 0.94 |
| Individual No. 15 | 0.72 | 3.37 | 3 | 2.18 | 6.21 |
| Individual No. 94 | 0.21  Onset | 0.98  Onset | 1.09 | 0.79 | 0.72 |
| Individual No. 902 | 1.97 | 0.97  Onset | 2.19 | 2 | 1.82 |

\* For the blood collection day, the delivery day is Day 0, and any day before delivery is expressed by minus (−).

In Table 2, the individual No. 94 had the onset of mastitis twice: once between the blood collection periods 1 and 2 and once between the periods 2 and 3. The individual No. 902 had the onset of mastitis once between the periods 2 and 3. In the present results, the individual No. 902 showed a phenomenon in which the proportion of CD11c$^+$ CD172a$^+$ blood dendritic cell gate 2 was decreased due to stress and the like at 8 to 10 days after delivery, probably thereby having the onset of mastitis. The individual No. 94 had a low proportion of CD11c$^+$ CD172a$^+$ blood dendritic cell gate 2 from before delivery, and thereafter had a not sufficiently higher proportion of the CD11c$^+$ CD172a$^+$ blood dendritic cell gate 2 (even when exposed to bacteria), probably thereby having the onset of mastitis. In contrast, the individuals receiving the administration of *Bacillus subtilis* strain C-3102 (individual Nos. 23 and 15) had a low proportion of CD11c$^+$ CD172a$^+$ blood dendritic cell gate 2 before delivery as is the case with the individual No. 94, but had a higher proportion of the CD11c$^+$ CD172a$^+$ blood dendritic cell gate 2 at 8 to 10 days after delivery, also resulting in the suppression of the onset of mastitis.

Example 2

<Characterization of *Bacillus subtilis* Effective for Prevention or Therapy of Mastitis>

Many viable bacteria agents for cows are currently known; however, no such agents shown to have a preventive or therapeutic effect against mastitis are known. The *Bifidobacterium*-growing activity, the protease activity, and the amylase activity of *Bacillus subtilis* strain C-3102 as the intended bacterium of the present invention were compared in this Example with those of bacterial strains in actually marketed viable bacteria agents.

(1) Bacterial Strain

For *Bacillus* strains, 8 strains of *B. subtilis*, 1 strain of *B. licheniformis*, and 2 strains of *Bacillus* sp. shown in Table 3 described later, including a difference in the shape of colonies were prepared.

(2) Preparation of Spore Suspension of Each Bacterium

Each bacterial strain was applied to TS agar medium and cultured at 37° C. overnight. All of the colonies formed on the medium were scraped with a spatula and suspended in sterilized water heated to 80° C. The resultant was centrifuged at 3,000 rpm and room temperature for 10 minutes and, after removing the supernatant, resuspended in sterilized water heated to 80° C. After performing the operation 2 times, the resultant was suspended in 5 ml of sterilized water to make a spore suspension of each bacterial strain.

(3) Measurement of Secreted Protease Activity

A 1% casein sodium TS agar medium (1% casein sodium (Wako Pure Chemical Industries, Ltd., Japan), 3% BBL Trypticase Soy Broth, 2% agar) was used to spot 1 µl of the spore suspension of each bacterial strain (about 1×10$^4$ CFU/ml) on the medium. Thereafter, culture was carried out at 37° C. for 48 hours, followed by measuring the size of the halo produced by the decomposition of casein around the colony. The size of the halo was obtained by measuring the distance from the edge of the colony to the edge of the halo. The experiment was carried out 3 times, and the average of 3 measured values and the average of values of specific activity relative to C-3102 strain Type I in the 3 experiments were calculated for each bacterial strain.

(4) Measurement of Amylase Activity

A 1% starch TS agar medium (1% starch (Wako Pure Chemical Industries, Ltd., Japan), 3% BBL Trypticase Soy Broth, 2% agar) was used to spot 1 µl of the spore suspension of each bacterial strain (about 1×10$^4$ CFU/ml) on the medium. After culture was carried out at 37° C. for 48 hours, 2 ml of Lugol's solution stabilized (Merck) was added dropwise on the medium to stain undegraded starch, thereby measuring the size of the halo produced around the colony. The size of the halo was obtained by measuring the distance from the edge of the colony to the edge of the halo. The experiment was carried out 3 times, and the average of 3 measured values and the average of values of specific activity relative to C-3102 strain Type I in the 3 experiments were calculated for each bacterial strain.

(5) *Bifidobacterium*-Growing Activity

In reference to the method described in a reference (i.e., Kouya T. et al., J. Biosci. Bioeng. 2007; 103: 464-471), the experiment was carried out as follows. A cellulose-mixed ester filter (90 mm diameter and 0.2 µm pore size (ADVANTEC)) was put on TS agar medium (agar: 0.75%), and 50 µl of the sore suspension (about 1×10$^9$ CFU/ml) was seeded on the filter and cultured at 37° C. for 24 hours. After culture, the filter was stripped off to recover the medium, which was then transferred to 50 ml of a centrifuge tube and subjected to centrifugation at 8,000 rpm for 15 minutes. The resultant supernatant was filtered with a 0.22-µm cellulose-mixed ester filter (ADVANTEC), and 60 µl of the filtrate was infiltrated into a paper disk (10 mm diameter, thick (ADVANTEC)) placed on TPY agar medium (3% glucose, 0.4% Trypticase peptone, 0.15% proteose peptone No. 3, 0.25% yeast extract, 0.2% K$_2$HPO$_4$, 0.3% KH$_2$PO$_4$, 0.025% MgCl$_2$ 6H$_2$O, 0.025% L-cystein, 0.0005% FeSO$_4$ 7H$_2$O, 1.5% agar) into which *Bifidobacterium adolescentis* CP2238 was poured. The resultant was subjected to anaerobic culture at 37° C. for 18 hours in an anaerobic jar in which 3 sheets of Anaero Pack (Mitsubishi Gas Chemical Co., Ltd.) were placed, and the diameter of a *Bifidobacterium* growth circle produced around the paper disk was measured. The experiment was carried out 2 times, and the average of 2 measured values and the average of values of specific activity relative to C-3102 strain Type I in the 2 experiments were calculated for each bacterial strain.

(6) Result

The results of measuring the tested bacteria are shown in Table 3.

silage, alfalfa hay cube) were provided during the lactation period, and a feed for the dry period (Trans-Pro, Snow Brand Seed Co., Ltd., Japan) and a coarse feed (timothy, oats) were provided during the dry period.

INDUSTRIAL APPLICABILITY

The present invention can achieve the prevention of onset or therapy of mastitis in ruminant animals, especially cows, such as dairy cows; thus, it can greatly reduce the economic

TABLE 3

| Isolated Strain from Commercial Product (colony) | Strain in Viable Bacteria Agent | Protease Activity Average Size of Halo (mm) | Score | Amylase Activity Average Size of Halo (mm) | Score | Bifidobacterium-Growing Capacity Average Size of Growth Circle (mm) | Score |
|---|---|---|---|---|---|---|---|
| Calsporin | *Bacillus Subtilis* Strain C-3102 | 9.7 | 1.0 | 3.5 | 1.0 | 35.5 | 1.0 |
| Commercial Product A-1 | *B. subtilis* | 1.0 | 0.10 | 1.2 | 0.34 | 29.0 | 0.82 |
| Commercial Product A-2 | *B. subtilis* | 8.0 | 0.82 | 2.7 | 0.77 | 28.2 | 0.79 |
| Commercial Product B | *B. subtilis* | 0.5 | 0.05 | 1.7 | 0.49 | 34.2 | 0.96 |
| Commercial Product C | *B. licheniformis* | 1.5 | 0.15 | 0.2 | 0.06 | 37.8 | 1.06 |
| Commercial Product D | *B. subtilis* | 7.3 | 0.75 | 2.2 | 0.63 | 35.3 | 0.99 |
| Commercial Product E | *B. subtilis* | 8.7 | 0.90 | 4.7 | 1.34 | 29.8 | 0.84 |
| Commercial Product F-1 | *Bacillus* sp. | 3.2 | 0.33 | 1.3 | 0.37 | 24.0 | 0.68 |
| Commercial Product F-2 | *Bacillus* sp. | 4.3 | 0.44 | 4.0 | 1.14 | 21.3 | 0.60 |
| Commercial Product G-1 | *B. subtilis* | 7.7 | 0.79 | 3.0 | 0.86 | 30.1 | 0.85 |
| Commercial Product G-2 | *B. subtilis* | 6.0 | 0.62 | 5.7 | 1.63 | 20.0 | 0.56 |

From Table 3, it was confirmed that *Bacillus subtilis* strain C-3102 had high activities on average for all the properties compared to those of the other bacteria. These properties indicate that they increase survival in the digestive tract of cows and, further, it seems that they enhance the growth of *Bifidobacterium* in the digestive tract and thereby contribute to increasing blood dendritic cells. As a result, strain C-3102 can suppress bacterial infection even when dairy cows are injured on the nipple or the like and prevents mastitis by suppressing the infection of the milk vessels, lactiferous ducts, or mammary glands in the breast even if the cows are infected with bacteria. In addition, the strain seems to also effectively work in the therapy of dairy cows affected with mastitis by increasing certain dendritic cells.

In fact, *Bacillus subtilis* strain C-3102 had a preventive or therapeutic effect against mastitis in dairy cows as described in Example 1, and *Bacillus subtilis* bacteria having the activities similar or comparable to those of the strain can be expected to have the capability to increase or maintain the dendritic cell gate 2 and can be expected to have an effect comparable to that of the strain C-3102.

Example 3

<Therapy of Dairy Cow Having Onset of Mastitis>

Calsporin™ (Calpis Co., Ltd., Japan) (active ingredient: *Bacillus subtilis* strain C-3102 (FERM BP-1096) $1 \times 10^{10}$ cells/g) was fed to dairy cows during the lactation period, having a history of mastitis when they had the onset of mastitis during the lactation period for a certain period of time (several days to 1 week) after onset by mixing the bacteria at a viable bacterial dose of $6 \times 10^9$ cells/day or more in a feed. As a feed, Rakunoh Kazoku Max (Zennoh Feed Mills of the Tohoku District Co, Ltd., Japan), Astroliner (vitamin preparation: Snow Brand Milk Products Co., Ltd.), flaked corn, and a coarse feed (timothy, oats, dent corn loss due to the onset of dairy cow mastitis in milk industry and can be said to be extremely high in industrial usefulness.

DEPOSITED BACTERIA

"*Bacillus subtilis* strain C-3102" was domestically deposited on Dec. 25, 1985 in International Patent Organism Depositary, National Institute of Advanced Industrial Science and Technology at Tsukuba Central 6, 1-1-1 Higashi, Tsukuba, Ibaraki, Japan (post code: 305-8566) [at deposit, 1-1-3 Higashi, Yatabe, Tsukuba, Ibaraki, Japan (post code: 305)] under Accession No. FERM P-8584, and has been transferred to the international deposit on Jun. 28, 1986 in the same institute under Accession No. FERM BP-1096 (at the time of transfer). The deposited strain is currently stored in the Patent Microorganisms Depositary, National Institute of Technology and Evaluation (NITE) (NITE-IPOD) (room 120, 2-5-8 Kazusakamatari, Kisarazu, Chiba, Japan (post code: 292-0818)).

What is claimed is:

1. A method for enhancing a preventive or therapeutic effect of a feed for female cows on cow mastitis, comprising:
   adding a feed additive for the prevention or therapy of cow mastitis to the feed for female cows, wherein the feed additive comprises, as an active ingredient, *Bacillus subtilis* strain C-3102 (international accession number: FERM BP-1096); and
   administering the feed to a female cow, for a period from 1 month before cow delivery to 3 months after the delivery, in an amount effective to prevent the development of cow mastitis in the female cow, or to treat cow mastitis if the female cow is affected with mastitis.

2. The method according to claim 1, wherein the female cow is a dairy cow.

3. The method according to claim 1, the feed additive further comprises an antibiotic for the therapy of mastitis.

4. The method according to claim 1, wherein the *Bacillus subtilis* strain C-3102 (international accession number: FERM BP-1096) is orally administered to the female cow at a dose of $1\times10^5$ cells/day/animal or more.

5. A method for the prevention or therapy of mastitis in a female cow, comprising administering a preventive or therapeutic agent to the female cow in need thereof for a period from 1 month before cow delivery to 3 months after the delivery, wherein the preventive or therapeutic agent comprises, as an active ingredient, *Bacillus subtilis* strain C-3102 (international accession number: FERM BP-1096), and the preventative or therapeutic agent is administered in an amount effective to prevent the development of mastitis in the female cow, or to treat mastitis if the female cow is affected with mastitis.

6. The method according to claim 5, further comprising administering an antibiotic for the therapy of mastitis, if necessary.

7. The method according to claim 5, wherein the *Bacillus subtilis* strain C-3102 (international accession number: FERM BP-1096) is orally administered to the female cow at a dose of $1\times10^5$ cells/day/animal or more.

8. The method according to claim 5, wherein the female cow is a dairy cow.

* * * * *